United States Patent [19]

Sugimoto et al.

[11] Patent Number: 4,883,577
[45] Date of Patent: Nov. 28, 1989

[54] ELECTROPHORESIS DEVICE WITH SHARK-TOOTHED COMB HAVING A THICKNESS DETERMINED BY THE THICKNESS OF THE GEL

[75] Inventors: Naohiko Sugimoto; Akira Fujita, both of Saitama, Japan

[73] Assignee: Fuji Photo Film Co., Ltd., Kanagawa, Japan

[21] Appl. No.: 174,467

[22] Filed: Mar. 28, 1988

[30] Foreign Application Priority Data

Mar. 30, 1987 [JP] Japan .................................. 62-76591
May 12, 1987 [JP] Japan ................................ 62-114959

[51] Int. Cl.$^4$ ............................................. G01N 27/28
[52] U.S. Cl. ............................... 204/299 R; 204/182.8
[58] Field of Search ......................... 204/299 R, 182.8

[56] References Cited

U.S. PATENT DOCUMENTS

| | | | |
|---|---|---|---|
| 3,450,624 | 6/1969 | Natelson | 204/182.8 |
| 4,294,684 | 10/1981 | Serwer | 204/299 R |
| 4,305,799 | 12/1981 | Schwarz | 204/182.1 |
| 4,737,260 | 4/1988 | Strathmann | 204/301 |

FOREIGN PATENT DOCUMENTS 2902247  8/1980  Fed. Rep. of Germany ... 204/299 R

OTHER PUBLICATIONS

Budowle et al., "Applications of Isoelectric Focusing in Forensic Serology", in *New Directions in Electrophoretic Methods*, pp. 143–145 (1987).

*Primary Examiner*—John F. Niebling
*Assistant Examiner*—Isabelle Rodriguez
*Attorney, Agent, or Firm*—Sughrue, Mion, Zinn, Macpeak & Seas

[57] ABSTRACT

An electrophoresis device comprises a gel membrane disposed within a space formed by a pair of sheets and a pair of spacers. A shark's teeth comb is disposed at an end of the gel membrane such that a plurality of triangular sample-pouring apertures are formed by its saw-like protrusions and the end of the gel membrane. The thickness of the shark's teeth comb d and the thickness of the gel membrane G satisfy the following relation:

$$G \times 1.1 < d < G + 50$$

in which unit is $\mu m$.

4 Claims, 2 Drawing Sheets

ELECTROPHORESIS DEVICE WITH SHARK-TOOTHED COMB HAVING A THICKNESS DETERMINED BY THE THICKNESS OF THE GEL

BACKGROUND OF THE INVENTION

1. Field of the Invention

This invention relates to an electrophoresis device for separating and analyzing high molecular materials, such as proteins and nucleic acids which can have an electric charge in a solution, based on differences in their molecular charges and in their molecular weights.

2. Description of the Prior Art

The electrophoresis technique has been widely known for separating and analyzing proteins, nucleic acids, their degradation products and the like based on differences in molecular charges and in molecular weights in a membrane-like medium such as gel membrane and filter paper containing a buffer.

In particular, technique for determining base sequences of radioactive-labeled nucleic acids by using autoradiography is important in the field of genetic technology. In the electrophoresis for this purpose, a base-specific reaction product (mixture) of a radioactive-labeled DNA or of a fragment of such a DNA is subjected to electrophoresis along the direction of electric field of electrophoresis medium. In general, a plurality of base-specific reaction products are migrated in parallel along the direction of electric field. After this electrophoresis, a plurality of rows of electrophoresis patterns are obtained as an autoradiographic image (autoradiogram). Then, base sequence determination is conducted by comparing and contrasting these patterns therebetween.

Heretofore, an experimenter of electrophoresis has had to prepare by himself a gel membrane consisting of starch, polyacrylamide, etc. on a flat substrate such as a glass plate on every occasion for electrophoresis. This work is quite troublesome and has been a heavy burden to the experimenter who uses electrophoresis. Recently, in order to reduce this burden, a sheet device prefabricated for electrophoresis has become commercially available in which two electrically-insulated, flexible, water-impervious sheets (support sheet and cover sheet) are disposed face to face sandwiching therebetween a spacer of a predetermined thickness at each end in the width direction thereof, and a gel membrane is contained within thus formed space as electrophoresis medium.

When such a device is used for electrophoresis, it is necessary to pour the sample liquid, which is to be subjected to electrophoresis, into the upper end of gel membrane (i.e. the end that is positioned at the upper portion of an upright electrophoresis apparatus and does not face the above-mentioned spacer) before beginning the electrophoresis. Accordingly, forming of a plurality of rectangular wells (or slots) each provided with an open end has widely been used in practice. This method, however, results in a gap of 1 mm or more formed between a pair of adjacent electrophoresis areas (lanes), corresponding to the interval between the adjacent wells. In the base sequence determination of a DNA, where electrophoretic images of fragments containing four kinds of bases (A, G, C, T), respectively, have to be compared and collated each other, such a gap between the lanes of electrophoresis images makes the collation difficult. It is therefore desirable that there is no or little distance between the electrophoresis lanes.

In order to fulfill this requirement, it has been known to dispose a so-called shark's teeth comb, which is a flat plate-like member having saw-like protrusions, such that it is in close contact with or partially intruded into an end of a gel membrane, and to pour a sample liquid into a substantially triangular space formed by the end of the gel membrane and a pair of adjacent end faces of the protrusions. If the thickness of the comb is equal to that of the gel membrane in this case, the sample liquid will often invade a neighboring lane across a partition of the comb after pouring the liquid before beginning electrophoresis. This phenomenon is likely to occur particularly when a sample liquid is poured into a lane after electrophoresis has been carried out using the adjacent lane for a few hours. In an extreme case, the comb may slip off from the position where it was fixed so that pouring of the sample liquid is impossible.

SUMMARY OF THE INVENTION

The object of the present invention is to provide an electrophoresis apparatus in which a shark's teeth comb can be fixed to an electrophoresis sheet element easily and securely, and in which a sample liquid is prevented from leaking in the vicinity of a liquid pouring portion.

The present invention provides an electrophoresis device in which a gel membrane adapted to function as electrophoresis medium is provided within a space formed between electrically-insulated, flexible, water-impervious support and cover sheets by means of spacers each having a predetermined thickness disposed between these sheets at an end in the width direction of the sheets, a plurality of sample-pouring apertures with partitions therebetween being formed at an end in the longitudinal direction of the gel membrane or in its vicinity inside the membrane. According to this invention, each sample-pouring aperture is composed of a substantially triangular space formed by an end of the gel membrane and adjacent end faces of saw-like protrusions of a shark's teeth comb which is disposed such that the protrusions are in contact with the end of the gel membrane. The thickness of the shark's teeth comb d and that of the gel membrane G are set to satisfy the following relation.

$$G \times 1.1 < d < G + 50$$

in which unit is $\mu m$.

In the above relation, G is less than 500 as a matter of course and generally within the range between 140 and 400 ($\mu m$).

Preferably, the thickness of the shark's teeth comb d satisfies the following relation:

$$G \times 1.1 < < d \leq G + 45$$

The thickness of the comb d may be slightly larger than the thickness of the spacer (which is generally thicker than the gel membrane by 10–15 $\mu m$) disposed between the support and cover sheets at an end thereof. However, it is desirable that the difference between their thicknesses does not exceed $+20\mu$ in order to secure insertion of the comb.

As material for the comb, thermoplastic synthetic or semisynthetic polymer is suitable, and polyethylene terephthalate film is preferable. Though transparent material may be used, semitransparent material is preferably used so that the liquid pouring apertures are easily discerned. (For example, Lumirror Film #250 S10, #250 H10 and the like manufactured by TO-RAY Co., Ltd. can be used preferably.)

The comb will be difficult to handle when it is too short, while it will be obstructed by a hand and the like when it is too long. Its length is desirably within the range of 30-40 mm. As a matter of course, its width is determined by the overall length of the sample pouring portion to be formed.

There is no particular limitation to the shape of protrusions (shark's teeth) of the comb. Accordingly, known combs can be used. In addition to those with pointed tips, such teeth as those shown in FIG. 1c can be used. In particular, a comb with shape described in Japanese Patent Application No. 61(1986)-190999 is preferable.

Various known materials can be used as electrophoresis medium. For example, an electrophoresis sheet device comprising polyacrylamide as electrophoresis medium described in Japanese Unexamined Patent Publication No. 61(1986)-18852 is preferable. The method and apparatus described in Japanese Unexamined Patent Publication No. 60(1985)-203847, for example, can be used for making such an electrophoresis sheet device. In addition to polyacrylamide gel, other materials such as agarose gel and starch can be used as electrophoresis medium used in the present invention.

Polyethylene terephthalate is preferably used as material for the support sheet, though polyethylene, polypropylene, polymethylmethacrylate and the like can also be used. Preferably, its surface is treated by various known methods to become hydrophilic. The same can be said as to material for the cover sheet.

A known upright electrophoresis apparatus can be used in accordance with the present invention. The apparatus described in Japanese Unexamined Patent Publication No. 61(1986)-278751 is one preferable example.

Glass plates are usually used for holding an electrophoresis sheet device therebetween to fix it to an electrophoresis apparatus. However, ceramics, quartz, transparent plastics and the like can also be used therefor. Tempered glass formed by heat treatment, chemical treatment and the like is preferable as glass plate in that it is hard to break or deform. Though a pair of plates can be made of different materials, they are preferably made of the same material. It is desirable that these plates have a flatness within the range of ±10 μm. A cutout is formed in one of these two plates to communicate a buffer tank to the electrophoresis gel membrane.

When the electrophoresis apparatus of the present invention is used, a sample liquid is prevented from invading the sample pouring aperture of the neighboring lane across the partition of the comb after pouring thereof before beginning electrophoresis. In particular, even in the case where a sample liquid is poured into the sample-pouring aperture of a lane after a few hour-long electrophoresis has been performed in the neighboring lane, leakage as described in the above does not occur. Also, the sample liquid does not invade a neighboring lane from between the cover sheet and the gel membrane.

DESCRIPTION OF THE PREFERRED EMBODIMENTS

Figure 1:
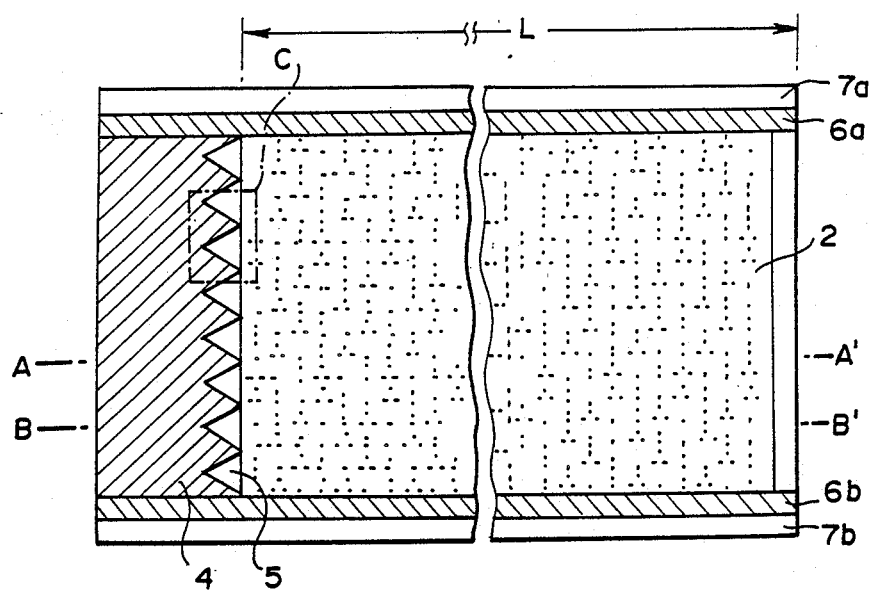
FIG. 1 is a decomposed plane view showing an embodiment of the electrophoresis device in accordance with the present invention from which the support sheet 3 is taken away.
Figure 1A:
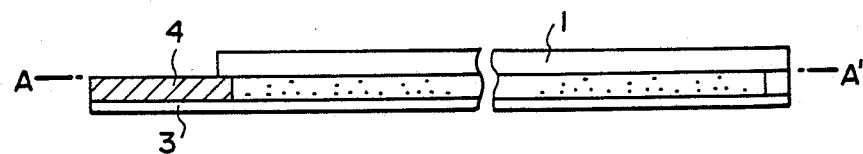
FIG. 1A is a sectional view of the device taken along the line A—A' of FIG. 1.
Figure 1B:
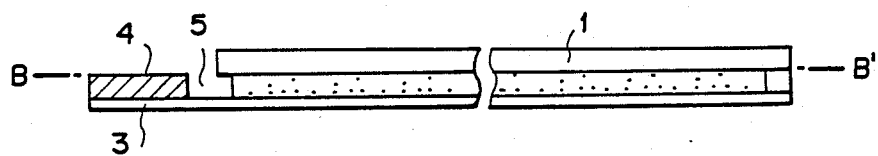
FIG. 1B is a sectional view of the device taken along the line B—B' of FIG. 1.
Figure 1C:
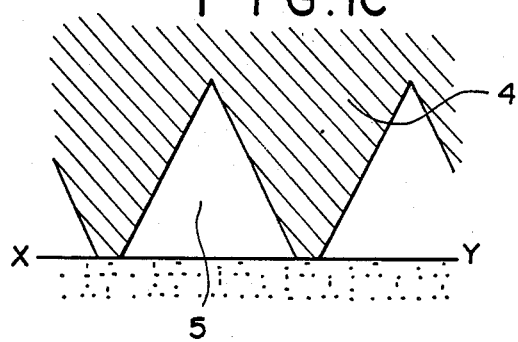
FIG. 1C is an enlarged plane view of the device in the area C of FIG. 1.
Figure 2:
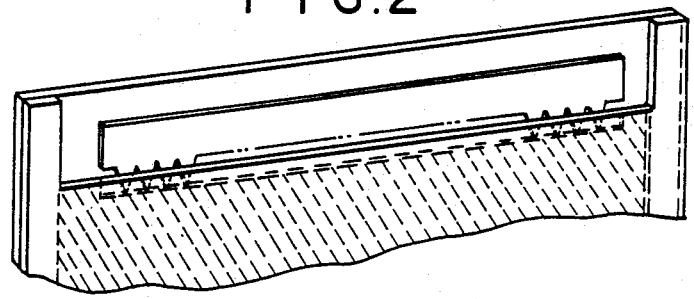
FIG. 2 is a perspective view showing a sample-pouring portion of the device in which a shark's teeth comb is inserted.
Figure 3:
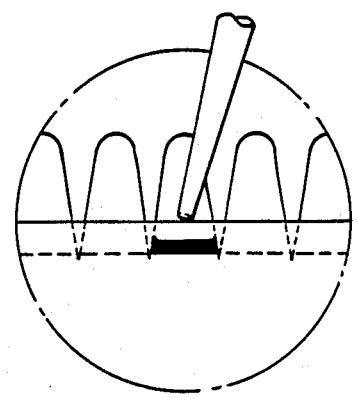
FIG. 3 is an enlarged view showing a state where a sample liquid is poured into a sample-pouring portion.

The present invention will hereinbelow be described in further detail with reference to the following Examples.

(Example 1)

(1) Preparation of Gel Membrane Composition 100 ml of an aqueous acrylamide solution containing the ingredients listed below was prepared.
acrylamide 7.6 g
N,N'-methylenebisacrylamide 0.4 g
buffer containing disodium hydrogenphosphate, sodium dihydrogenphosphate and tris(hydroxymethyl) aminomethane To this solution, a polymerization initiator comprising the ingredients listed below was added.
ammonium peroxodisulfate 65 mg
tetramethylethylenediamine 33 μl.
sodium riboflavin phosphate ester 10 mg.

(2) Preparation of Electrophoresis Sheet

To each end of a polyethylene terephthalate (PET) film web having a thickness of 175 μm and a width of 20 cm (which serves as a support sheet), a tape-like spacer having a thickness of 250 μm and a width of 10 mm made of polyethylene terephthalate was attached. The above-prepared gel membrane composition was extended over a concave portion formed between the spacers with a thickness of 210 μm, and then crosslinkingly polymerized by ultraviolet radiation under a nitrogen atmosphere to obtain a polyacrylamide gel membrane.

Thereafter, this web was cut to a length of 40 cm. A part of the gel was linearly cut off 24 mm from a longitudinal end of thus cut web to expose the PET film. A cutout having a width of 130 mm is formed in the exposed part of the PET film to reach 20 mm inside from the edge of the web. Then, a cover sheet made of PET having a thickness of 63 μm and the same size as that of the support sheet is provided thereover to form an electrophoresis medium sheet. For comparison, an electrophoresis medium sheet ("Comparative Sheet") was provided with a plurality of rectangular cutout portions each having a width of 5 mm and a length of 5 mm with a space of 1.5 mm therebetween at an end of the gel membrane (24 mm inside from the edge of the cover sheet), instead of linearly cutting off the gel from a longitudinal end of the gel sheet.

(3) Insertion of Shark's Teeth Comb

By using each of thus obtained electrophoresis sheets, an electrophoresis device as shown in FIG. 1 was constructed.

A shark's teeth comb having a thickness of 250 μm shown in FIG. 1 was inserted into an end of the gel membrane of the electrophoresis sheet (the portion where only the gel was linearly cut off) in order to form partitions for sample-pouring apertures (each aperture having a maximum width of 4.5 mm, each partition having a minimum width of 0.2 mm), thereby completing making of an electrophoresis device according to the present invention. (No comb was inserted into the Comparative Sheet.)

(4) Electrophoresis and Autoradiography

DNA samples in accordance with Sanger method labeled with 32p were poured into the sample pouring apertures of the above-mentioned two types of electrophoresis devices by using a microsyringe. After electrophoresis on each gel membrane, autoradiography was performed to obtain an electrophoretic image thereof.

In the electrophoretic image obtained by the electrophoresis device of the present invention using the specified shark's teeth comb, vertical relationship of recorded bands was easy to see since neighboring bands were close to each other. Accordingly, the number of discernible (readable) bases was greater than that in the Comparative Device.

Further, for the purpose of comparison, an electrophoresis device was formed with a shark's teeth comb having a thickness of 210 μm (the same thickness as the gel membrane). When the same operation as mentioned above was conducted, the sample liquid usually invaded a neighboring lane. Accordingly, no base sequence could be read from the electrophoretic image.

(Example 2)

A polyacrylamide gel was obtained in the same manner as Example 1 except that it was formed to have a thickness of 200 μm by using a 230 μm-thick spacer. A shark's teeth comb having a thickness of 230 μm (each sample-pouring aperture having a width of 5 mm, each partition having a width of 0.5 mm) was inserted therein to obtain an electrophoresis device in accordance with the present invention.

As in the case of Example 1, a comparative electrophoresis device having rectangular gutter-like sample-pouring apertures was prepared.

Electrophoresis was conducted by using DNA Samples in accordance with Sanger method labeled with 35S in the same manner as Example 1. The number of discernible (readable) basis in thus obtained electrophoretic image was greater than that in the comparative electrophoresis device having rectangular gutter-like sample-pouring apertures without a shark's teeth comb, since neighboring bands were closer to each other.

Further, for the purpose of comparison, the same operation as described in the above was conducted by using a shark's teeth comb having a thickness of 250 μm (the thickness of gel membrane plus 50 μm). In this case, the sample liquid invaded a part of the gel membrane in the periphery of the sample-pouring aperture, and thereby a blurred electrophoresis image was obtained.

We claim:

1. An electrophoresis device, comprising:
  a pair of electrically-insulated, flexible, water-impervious sheets disposed in an opposing relationship to one another;
  spacers disposed between said sheets for separating said sheets, said spacers having a predetermined thickness;
  gel membrane disposed between said sheets adapted to function as an electrophoresis medium;
  a combo disposed adjacent an end of said gel membrane, said comb having a plurality of saw-like protrusions abutting said end of said gel membrane so as to define a plurality of sample-pouring apertures, each of said apertures having a substantially triangular space formed by said end of said gel membrane and adjacent end faces of said saw-like protrusions, wherein the thickness of said shark's teeth comb d and the thickness of said gel membrane G satisfy the following equation:

$$G \times 1.1 < d < G + 50$$

in which the units are in micrometers.

2. An electrophoresis device as defined in claim 1 in which said shark's teeth comb comprises polyethylene terephthalate.

3. An electrophoresis device as defined in claim 1 in which said shark's teeth comb comprises semitransparent polyethylene terephthalate.

4. An electrophoresis device as defined in claim 1 in which said spacers are thicker than said gel membrane, and the difference between the thickness of said shark's teeth comb d and the thickness of said spacer does not exceed +20 μm.

* * * * *

UNITED STATES PATENT AND TRADEMARK OFFICE
CERTIFICATE OF CORRECTION

PATENT NO. : 4,883,577

DATED : NOVEMBER 28, 1989

INVENTOR(S) : SUGIMOTO ET AL.

It is certified that error appears in the above-identified patent and that said Letters Patent is hereby corrected as shown below:

Column 6, line 23, change "combo" to --comb--.

line 28, change "sald" to --said--.

Signed and Sealed this

Twelfth Day of February, 1991

Attest:

HARRY F. MANBECK, JR.

Attesting Officer

Commissioner of Patents and Trademarks